US010765602B1

(12) United States Patent
Arnett et al.

(10) Patent No.: US 10,765,602 B1
(45) Date of Patent: Sep. 8, 2020

(54) MEDICATION DELIVERY SYSTEMS AND METHODS

(71) Applicant: Eli Lilly and Company, Indianapolis, IN (US)

(72) Inventors: Jaime Ray Arnett, Fishers, IN (US); Andrew Thomas Snow, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/578,498

(22) Filed: Sep. 23, 2019

Related U.S. Application Data

(60) Provisional application No. 62/826,093, filed on Mar. 29, 2019.

(51) Int. Cl.
*A61J 1/14* (2006.01)
*A61K 9/14* (2006.01)
(Continued)

(52) U.S. Cl.
CPC .............. *A61J 1/1425* (2015.05); *A61K 9/14* (2013.01); *A61K 38/28* (2013.01); *A61M 11/00* (2013.01)

(58) Field of Classification Search
CPC .... A61J 1/1425; A61K 9/14; A61M 2202/062
See application file for complete search history.

(56) References Cited

U.S. PATENT DOCUMENTS

D248,373 S 7/1978 Allen
4,615,463 A 10/1986 Price et al.
(Continued)

FOREIGN PATENT DOCUMENTS

CN 102101557 6/2011
EM 005256419-0001 3/2018
(Continued)

OTHER PUBLICATIONS

"Activ-vial Portfolio" webpackaging .com Modified Jan. 16, 2017. Accessed Aug. 31, 2018. Available online at URL: <https:// www.webpackaging.com/en/portola/captechnologiesinc/assets/11431346/activ-vial-portfolio/>(Year: 2017).
(Continued)

*Primary Examiner* — Brandy S Lee
*Assistant Examiner* — Nidah M Hussain
(74) *Attorney, Agent, or Firm* — M. Daniel Spillman

(57) ABSTRACT

The present disclosure relates to a medication delivery system including a medication administration device, a medication within the medication administration device, a container defining a cavity receiving the medication administration device, and a cap attached to the container and sealing the medication administration device within the cavity. The medication administration device includes an actuator extending from a body and operable to expel the medication by depressing the actuator into the body. The cap includes hold down members positioned to bear against the body of the medication administration device to prevent movement of the medication administration device toward the cap beyond a predetermined distance. The medication administration device is thereby prevented, inter alia, from prematurely discharging the medication during storage and transport.

23 Claims, 7 Drawing Sheets

(51) Int. Cl.
*A61M 11/00* (2006.01)
*A61K 38/28* (2006.01)

(56) References Cited

U.S. PATENT DOCUMENTS

| | | | |
|---|---|---|---|
| D332,739 S | 1/1993 | Petschek | |
| 5,788,064 A | 8/1998 | Sacherer et al. | |
| 6,130,263 A | 10/2000 | Hekal | |
| 6,158,607 A | 12/2000 | Wallberg | |
| D555,490 S | 11/2007 | Liu | |
| D564,841 S | 3/2008 | Clemens et al. | |
| 7,413,083 B2 | 8/2008 | Belfance et al. | |
| 7,434,689 B2 | 10/2008 | Homann | |
| D606,368 S | 12/2009 | Wu | |
| D616,608 S | 5/2010 | Maddy | |
| D618,362 S | 6/2010 | Giraud et al. | |
| D633,800 S | 3/2011 | Haywood | |
| D641,088 S | 7/2011 | Giraud et al. | |
| 8,051,998 B1 | 8/2011 | Giraud et al. | |
| D677,396 S | 3/2013 | Belfance et al. | |
| D679,583 S | 4/2013 | Wada et al. | |
| D688,563 S | 8/2013 | Cohen et al. | |
| D694,100 S | 11/2013 | Schneider et al. | |
| 8,771,711 B2 | 7/2014 | Kamishita et al. | |
| 8,915,393 B2 | 12/2014 | Hayton et al. | |
| D722,273 S | 2/2015 | Ivie | |
| D728,376 S | 5/2015 | Floyd et al. | |
| D750,965 S | 3/2016 | Alvarez De Cienfuegos Hernandez et al. | |
| D793,818 S | 8/2017 | Debretton Gordon | |
| D804,319 S | 12/2017 | Galekovic | |
| D816,514 S | 5/2018 | Wolfson et al. | |
| D821,204 S | 6/2018 | Reggiani et al. | |
| D822,498 S | 7/2018 | Sutcliffe | |
| D827,388 S | 9/2018 | Kander | |
| D835,509 S | 12/2018 | Cowan | |
| D837,059 S | 1/2019 | Wiggins | |
| D841,398 S | 2/2019 | Gauss et al. | |
| D856,798 S | 8/2019 | Giraud et al. | |
| 2006/0071027 A1 | 4/2006 | Davies et al. | |
| 2006/0219727 A1 | 10/2006 | Giraud | |
| 2007/0045358 A1 | 3/2007 | Arancibia | |
| 2007/0084735 A1 | 4/2007 | Lancesseur et al. | |
| 2007/0170193 A1 | 7/2007 | Schorner | |
| 2008/0283530 A1 | 11/2008 | Lee | |
| 2009/0095699 A1 | 4/2009 | Milante | |
| 2009/0241949 A1* | 10/2009 | Smutney | A61M 15/002 128/203.15 |
| 2010/0044252 A1 | 2/2010 | Portier et al. | |
| 2011/0062176 A1 | 3/2011 | Lourenco et al. | |
| 2011/0089187 A1 | 4/2011 | Steiger et al. | |
| 2011/0127269 A1 | 6/2011 | Bucholtz et al. | |
| 2012/0009356 A1 | 1/2012 | Choi et al. | |
| 2014/0000602 A1 | 1/2014 | Herder et al. | |
| 2014/0334804 A1 | 11/2014 | Choi | |
| 2014/0352707 A1 | 12/2014 | Liu | |
| 2015/0090711 A1 | 4/2015 | Peterson | |
| 2016/0257450 A1 | 9/2016 | Niggel | |
| 2016/0271320 A1 | 9/2016 | Le Maner | |
| 2017/0043914 A1 | 2/2017 | Belfance et al. | |
| 2018/0118423 A1 | 5/2018 | Bois et al. | |
| 2019/0039804 A1 | 2/2019 | Freedman et al. | |

FOREIGN PATENT DOCUMENTS

| | | |
|---|---|---|
| EP | 2439147 | 4/2012 |
| WO | 1996033108 | 10/1996 |
| WO | 2002028736 | 4/2002 |
| WO | 2010066510 | 6/2010 |
| WO | 2014014160 | 1/2014 |
| WO | 2016168400 | 10/2016 |

OTHER PUBLICATIONS

Lilly Aquires Locemia's Faster and Easier to use intranasal Glucagon, diaTribe, Oct. 9, 2015; Available online at URL: https://www.diatribe.org/locemias-intransal-glucagon-faster-and-easier-use-new-study.

Patent Cooperation Treaty International Search Report pertaining to International Application No. PCT/US2019/052332; International Filing Date: Sep. 23, 2019; dated Jan. 8, 2020.

Patent Cooperation Treaty Written Opinion of the International Searching Authority pertaining to International Application No. PCT/US2019/052332; International Filing Date: Sep. 23, 2019; dated Jan. 8, 2020.

* cited by examiner

MEDICATION DELIVERY SYSTEMS AND METHODS

TECHNICAL FIELD

This disclosure relates to medication delivery systems which provide for maintaining a medication administration device and contained medication in a viable condition. The disclosure further pertains to medical delivery systems in which the medication administration device may be quickly and easily removed from the container assembly for use.

BACKGROUND

Medication systems including medication administration devices with contained medications need to be maintained in proper conditions from the time the medication administration device is filled with the medication to eventual use by a patient. There is a particular need for such delivery systems which enhance the viability of pre-filled medication administration devices during storage and transport. Medication administration devices of this type are susceptible to a variety of quality issues. For example, the US Food and Drug Administration (FDA) recently issued draft guidance on quality considerations for aerosol drug delivery systems. See, wwwfda.gov/downloads/Drugs/GuidanceCompliance-RegulatoryInformation/Guidances/UCM070573.pdf (April, 2018). The guidance provides recommendations for the development and manufacture of aerosols. The guidance addresses quality profiles that include elements such as stability, dosage form, aerodynamic performance, and the delivery system. All of these aspects impact the utility of the dispensed medication.

In a particular aspect, the disclosed medication delivery system is used in connection with the delivery of glucagon. Normally, glucagon is produced in the pancreas and works with insulin to regulate blood glucose levels in the body. Glucagon is released in the body when blood glucose levels are low, signaling the liver to release glucose into the blood. People with diabetes either no longer produce insulin (Type 1) or their bodies are less able to respond to insulin (Type 2).

Both the medication administration device and the medication need to be provided in a manner that materially enhances the safety and efficacy of the dispensed medication. The medication may be provided with a stable environment to maintain proper moisture content, aerodynamic particle size distribution, and/or activity. The medication administration device may be maintained under proper conditions. Medication administration devices can be retained in a hermetically sealed enclosure prior to use. This can inhibit contact with moisture, foreign particulate matter, impurities, degradants, and other deleterious materials which might impair the proper functioning of the medication administration device. The medication administration devices should also be protected from physical damage and premature actuation.

While insulin and insulin pumps have evolved into highly technical and effective tools for treating diabetes, the methods for delivering emergency glucagon to save the lives of people with diabetes experiencing hypoglycemia have not progressed as far as desirable. Reconstituting powdered glucagon and injecting it can be difficult, and often the person with diabetes needs assistance. A simple nasal spray allows glucagon to be administered quickly and easily in a rescue situation.

For those with Type 1 diabetes (T1D), too much insulin can limit the body's ability to release glucagon as blood glucose levels fall; thus, if the person with T1D is unable to eat or drink sugar, treatment with glucagon is needed to bring blood glucose levels back into balance. Severe hypoglycemia can lead to hospitalization or even death in extreme cases. Maintaining the integrity of both the glucagon and its delivery device is therefore understood to be of great importance.

SUMMARY

In accordance with an aspect of the present disclosure, a medication delivery system is provided which comprises a medication administration device, medication received within the medication administration device, a container defining a cavity to receive the medication administration device, and a cap to seal the medication administration device within the container. The medication administration device is of a type in which an actuator extends from a body and is movable from the extended position to a depressed position to expel the medication. The container defines an access opening to a cavity into which the medication administration device is placed. A cap is secured to the container in the closed position to form a hermetic sealing of the medication administration device within the cavity. The cap includes one or more hold down members which are position to prevent the medication administration device from moving against the cap.

In another aspect, a training system includes a training module that is configured to simulate the medication delivery device, but does not contain a medication product, and/or a training container configured to simulate operation of the product container.

It is an object to provide a cap and container assembly which provides a secure and sealed enclosure for the medication administration device, while also including components which prevent premature discharge of the medication.

Another object is to provide a medication delivery system which contains a medication administration device in a manner that the medication administration device can be readily and quickly removed from a container for use.

Methods for the containment of medication administration devices in a manner to maintain the operability of the medication administration device and the viability of the contained medication are also disclosed.

Other objects and advantages of the disclosed medication delivery system will be apparent to those of ordinary skill in the art.

BRIEF DESCRIPTION OF THE DRAWINGS

The features and advantages of the present disclosure will become more apparent to those skilled in the art upon consideration of the following detailed description taken in conjunction with the accompanying figures.

DETAILED DESCRIPTION

Figure 1:
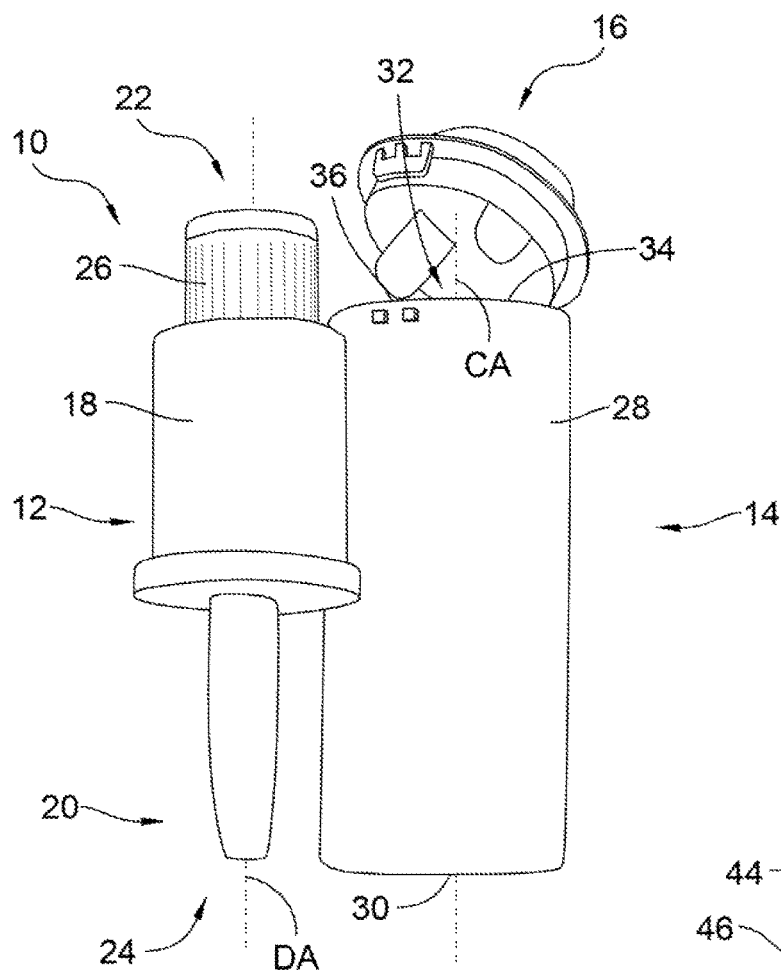
FIG. 1 is a perspective view of components useful in conjunction with a medication delivery system, depicting a medication administration device and a container in a side-by-side relationship.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

In one aspect there are disclosed intranasal delivery systems comprising a medication administration device for dispensing a medication. Such medication administration devices typically include a body containing a medication reservoir communicating through a discharge port, and an actuator mechanism for expelling the medication through the discharge port. The discharge port is sealed prior to use. The actuator is operable to unseal the discharge port and cause delivery of the medication. A common configuration for such a medication administration device includes an actuator that extends from the body prior to delivery of the medication. Moving the actuator from the extended position to a depressed position unseals the discharge port and releases the medication.

In an embodiment, there is disclosed a medication delivery system comprising a medication administration device, medication received within the medication administration device, a container receiving the medication delivery system, and a cap sealing the medication delivery system within the container. In another embodiment, there is provided a method for containing a medication administration device in a sealed condition protecting a contained medication. In yet another embodiment, there is provided a container assembly for a medication administration device including a container having an internal cavity for receiving the medication administration device, and a cap attached to the container and sealing the internal cavity in a closed position.

Referring to FIG. 1, there is shown an exemplary medication delivery system 10 comprising a medication administration device 12 containing a medication (not shown), a container 14 for receiving medication administration device 12, and a cap 16 for sealing container 14. Medication administration device 12 comprises a body 18 disposed generally longitudinally along a device axis DA, having a discharge end 20 and an opposed actuator end 22. The medication administration device includes a medication reservoir defined by body 18 and containing a medication to be dispensed from the medication administration device. The medication is dispensed through a medication discharge port 24 which comprises an opening communicating with the medication reservoir.

Medication administration device 12 further includes an actuator 26 for ejecting the medication from the reservoir through discharge port 24. Actuator 26 extends out of the actuator end of body 18. Actuator 26 further is linearly movable from an extended position shown in FIG. 1 to a depressed position (not shown). Medication discharge port 24 is sealed from communication with the medication reservoir when actuator 26 is in the extended position to retain the contained medication in a sealed condition. Actuator 26 is operable to discharge medication from the reservoir upon axial movement from the extended position to the depressed position. During such movement, communication between the discharge port and the reservoir is provided to allow for dispensing of the medication.

Also shown in FIG. 1 are the container 14 and cap 16. Container 14 has a tubular side wall 28 disposed longitudinally along a container axis CA. Side wall 28 is closed by bottom wall 30 at one end to define a cavity 32 within container 14. The opposed end provides an access opening 34 defined by end wall portion 36. Cavity 32 is sized and configured to receive medication administration device 12 with discharge end 20 adjacent bottom wall 30. Side wall 28 may generally define a cylindrical shape.

Cap 16 is sized and configured to mate with container 14 in the closed position to provide a hermetic seal enclosing cavity 32 for medication administration device 12 when received therein. Cap 16 includes one or more hold down members (described later with reference to FIG. 2) positioned and configured to bear against a non-actuator portion of body 18 of medication administration device 12. The one or more hold down members retain the medication administration device in the cavity 32 without pressure being applied to actuator 26 while cap 16 is in the closed position. In particular, each of the hold down members comprises a projection extending from cap 16 toward bottom wall 30. In one example, each of the hold down members is formed integrally from the same material with the cap using a molding process. In other examples, the hold down members may be formed separately and bonded or otherwise securely fixed to the cap. The hold down members may be made from a material that provides a rigid structure. In one example, rigid hold members are configured to maintain their relative orientation and positioning relative to the cap (and each other if more than one) and the non-actuator portion of body 18 of medication administration device 12 to avoid movement of the ends of the hold down members to an undesirable position that could cause premature actuation of the device. A rigid hold member can maintain its relative axial position and radial position of the members ends relative to the cap and the device.

Figure 2:
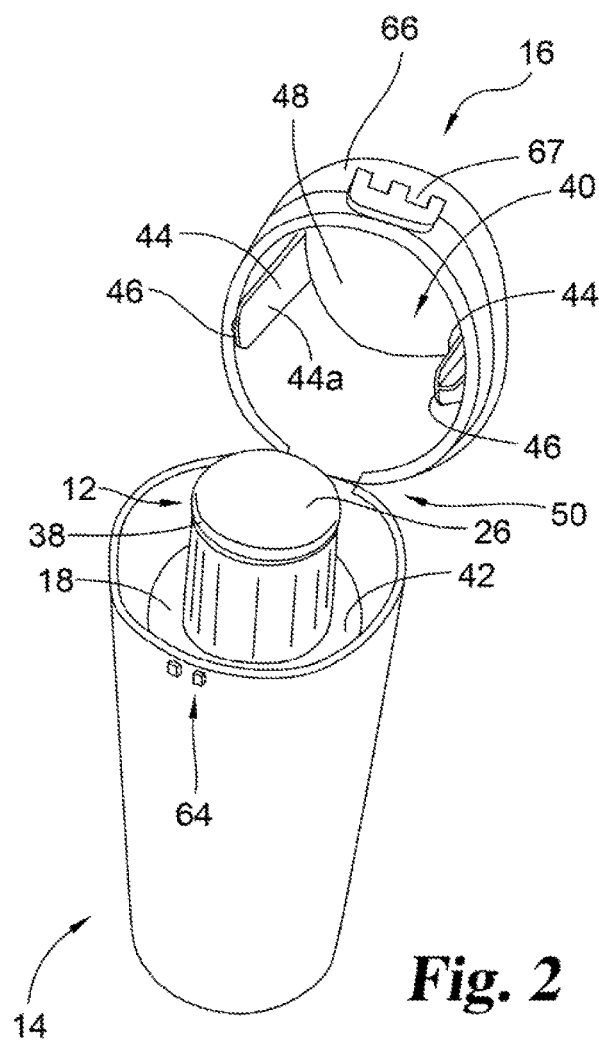
FIG. 2 is a perspective view of an embodiment of the medication delivery system, depicting the device inserted within the container with the cap in an open position.
Figure 3:
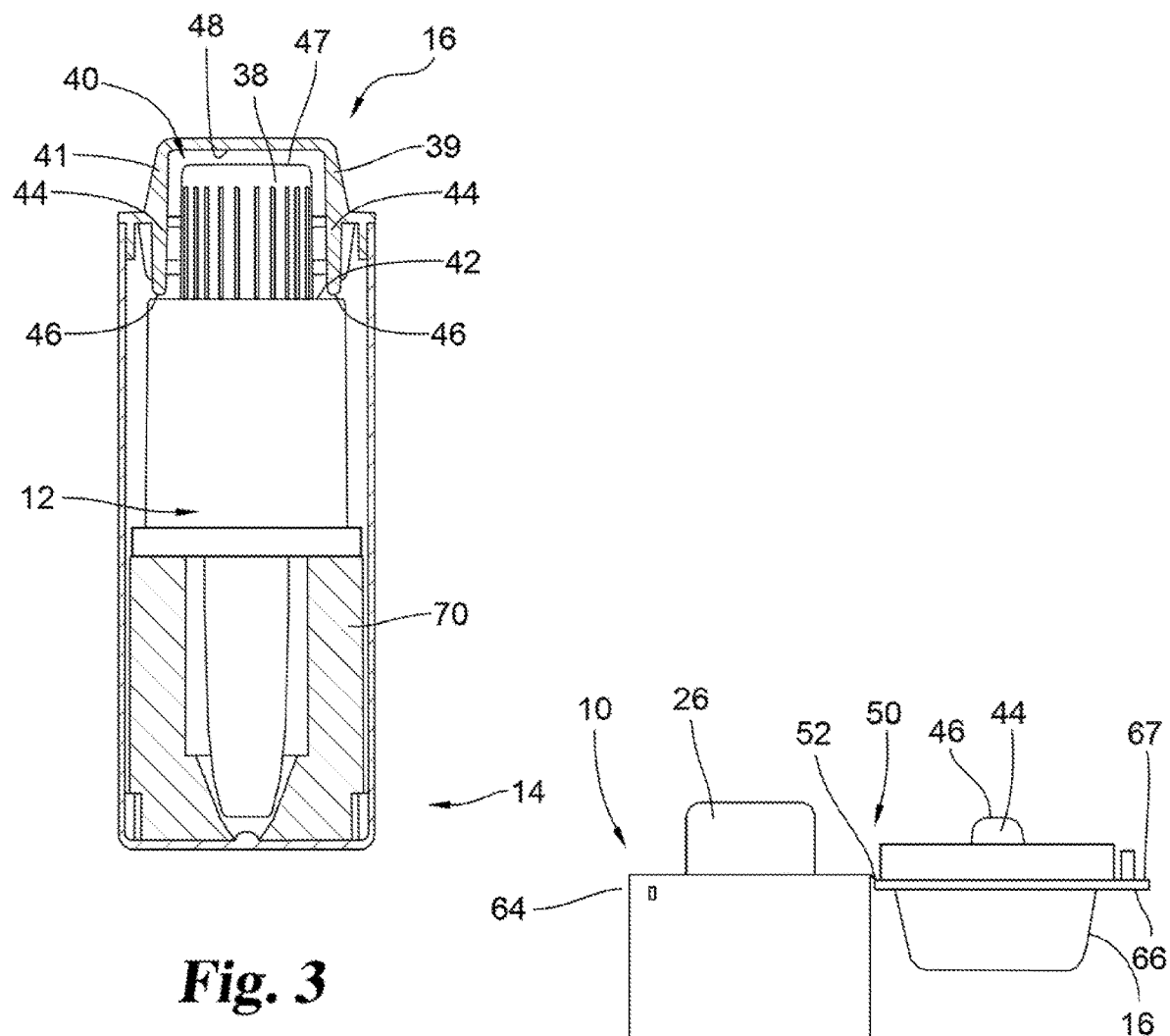
FIG. 3 is a side, cross-sectional view of the container of the medication delivery system of FIG. 2 with the device inserted.

Medication administration device 12 is shown received within container 14 in FIGS. 2-3. Actuator 26 is shown extending axially out of body 18 of medication administration device 12. At least an end portion 38 of actuator 26 extends beyond the plane of end wall portion 36. Cap 16 may include a cup shaped body 39 having a cap side wall 41 that defines a recess 40 receiving end portion 38 of actuator 26. The cup shaped body 39 of cap 16 may include a radially outward rim portion 66.

In FIG. 2, body 18 of medication administration device 12 includes a circumferential surface 42 surrounding, and coaxial with, actuator 26 about device axis DA and facing in the direction away from bottom wall 30. The hold down members 44 are shown in FIGS. 2-3 to be axially extending along the container axis CA when the cap is in the closed position. In one embodiment, there are two hold down members 44 extending from cap 16. The hold down members are configured to have end contact surfaces 46 positioned to bear against circumferential surface 42, representing the non-actuator portion, that is radially outside and clear of the actuator, in the event that medication administration device 12 is urged to move axially in a direction away from bottom wall 30. With a rigid hold member, the end contact surface 46 maintains its relative axial position and radial position relative to the cap and the circumferential surface 42 of the device. Movement of the end contact surface 46 from a structure having a spring configuration may permit the end contact surfaces to inadvertently cause premature actuation of the device. In one embodiment, shown in FIG. 7, an interior surface 41a of the cap side wall 41 and an interior surface 44a of the hold down members 44 define a continuous surface, and in some instances, a continuously smooth surface. The hold down members 44 may include a support rib along the radially outer surface of the hold down member. Other portions of the device may be used as the non-actuator portion that is contacted by the hold down members.

The relative positioning of the components is evident in FIG. 3. The one or more hold down members are provided to prevent the medication administration device from moving away from bottom wall 30 a distance that would cause end portion 38 of actuator 26 to bear against the interior axial surface 48 of cap 16. If such contact was allowed, it would be possible for the medication administration device to be damaged or to prematurely discharge the medication.

The one or more hold down members are positioned and configured to interfere with movement of the medication administration device to allow at most a predetermined amount of movement of the medication administration device in the direction away from bottom wall 30 and toward cap 16. It is not required that end contact surfaces 46 be engaged with circumferential surface 42 at all times. Rather, a slight gap can be provided between end contact surfaces 46 and circumferential surface 42 when the components of the medication delivery system are in an at rest position. If an external force is applied that would cause medication administration device 12 to move away from bottom wall 30, then the contact surfaces 46 of hold down members 44 serve as an end stop to such movement.

In this respect, as shown in FIG. 3, a small gap is provided between the contact surfaces 46 and the surface 42 of body 18. There is also a larger gap between the end surface 47 of end portion 38 and the interior surface 48 of cap 16. This relative sizing of the two gaps prevents the interior surface 48 from contacting the actuator 26. The smaller gap may, for example, be between 0.1 mm and 1.865 mm.

Figure 4:
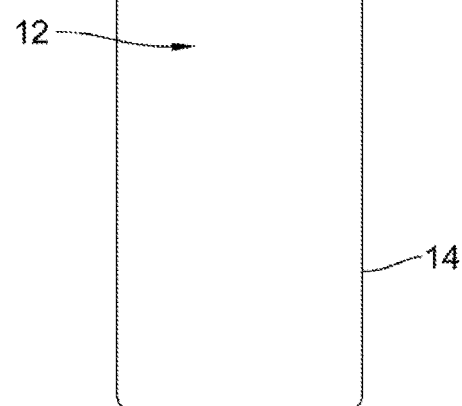
FIG. 4 is a side, elevational view of the medication delivery system of FIG. 2, showing the hinged connection of the cap with the container.
Figure 5:
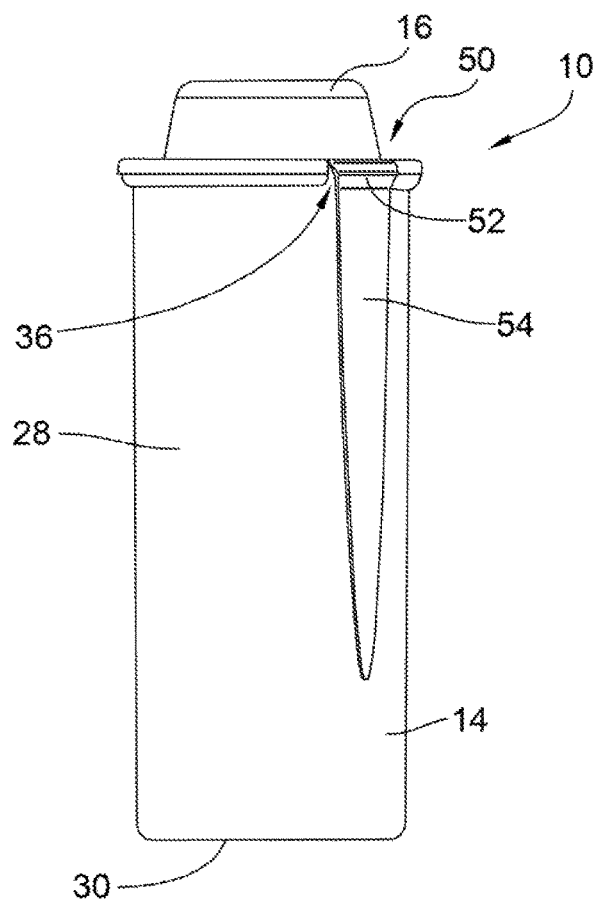
FIG. 5 is a side, elevational view of the container with the cap in a closed position, showing additional details of a living hinge.

With reference FIGS. 4-5, cap 16 may be joined to container 14 with a hinged connection 50. Connection 50 may be in the form of a "living hinge" comprising a continuous material bridge 52 integrally connecting cap 16 and container 14. FIG. 5 shows an external view regarding the hinged connection. An enlarged, axially-extending portion 54 of side wall 28 extends to end wall portion 36 to provide a living hinge 52. Portion 54 is flat, instead of matching the radius of wall 28. If the hinge is not straight, it will result in high stress on the ends of the hinge. This hinge design is intended to minimally vary the shape of the outside of the container for improved appearance. Other common hinges would result in a portion of the hinge protruding from wall 28. In this embodiment the cap and container are formed as one integral piece such as by injection molding.

Various embodiments of suitable hinges are known. For example, in an alternative embodiment the hinge comprises an axle-like member extending horizontally along the outside of the container. The axle is held at a position spaced from the exterior of the container wall, such as by a pair of outwardly extending flanges. In this embodiment, the cap includes a partially-cylindrical member that is received over and pivots around the axle. Alternatively, these structures may be reversed with the cap including the pivot axle and the container including the cylindrical component. In these alternate embodiments the cap and container would be formed separately and assembled together.

The two hold down members are disposed circumferentially away from one another, and the hinged connection 50 is disposed circumferentially between the two hold down members (44). In an exemplary embodiment, cap 16 includes two hold down members 44 positioned in opposed orthogonal positions, that is, about ninety degrees, relative to hinged connection 50. This provides two points of contact between hold down members 44 and body 18. The hold down members may extend from the cup shape body of the cap at radially opposite sides of the cap. In some examples, this can be diametrically opposite. In other examples, need not be directly radially opposite, but can be offset by, for example, 150 degrees. The relative positioning of the hold down members also makes it easier for the hold down members to "clear" side wall 28 and actuator 26 as cap 16 is moved between an open position and a closed position. However, it will be appreciated that any number and positioning of hold down members 44 may be used. It will also be appreciated that cap 16 need not be hingedly connected to container 14, and that in itself may require or allow different configurations of one or more hold down members.

In another exemplary embodiment, the cap includes a hinge joining the cap to the container. In one aspect, the cap only includes a single hold down member which can be disposed along any position from the interior of the cap. In one embodiment, the single hold down member is positioned interior of and radially aligned with the hinge, providing a good containment of the medication delivery device within the container. In another embodiment, the single hold down member may be positioned in either location of any one of the hold down members shown in, for example, FIG. 2, or, for example, positioned in the location of the one shown in FIG. 9.

Alternatively, cap 16 may be fully detachable from container 14. However, an advantage of the hinged connection is that it facilitates attachment and removal of cap 16. It also orients the hold down members in a desirable position relative to container 14.

Regardless of the manner of attachment of cap 16 with container 14 in the closed position, the provision of the hold down members as a part of the cap provides distinct advantages. Hold down members 44 are made available to retain the medication administration device while attached to the cap that is removed when the medication administration device is needed. Therefore, the removal of cap 16 also results in a removal of the hold down members, without requiring a separate action to unlock the medication administration device from the container. This allows for quick and easy removal of the medication administration device from the container. Although not required, the hold down members may also be provided as an integral component of cap 16, which facilitates production of the hold down members and avoids additional production steps and costs if provided as a separate component.

Figure 6:
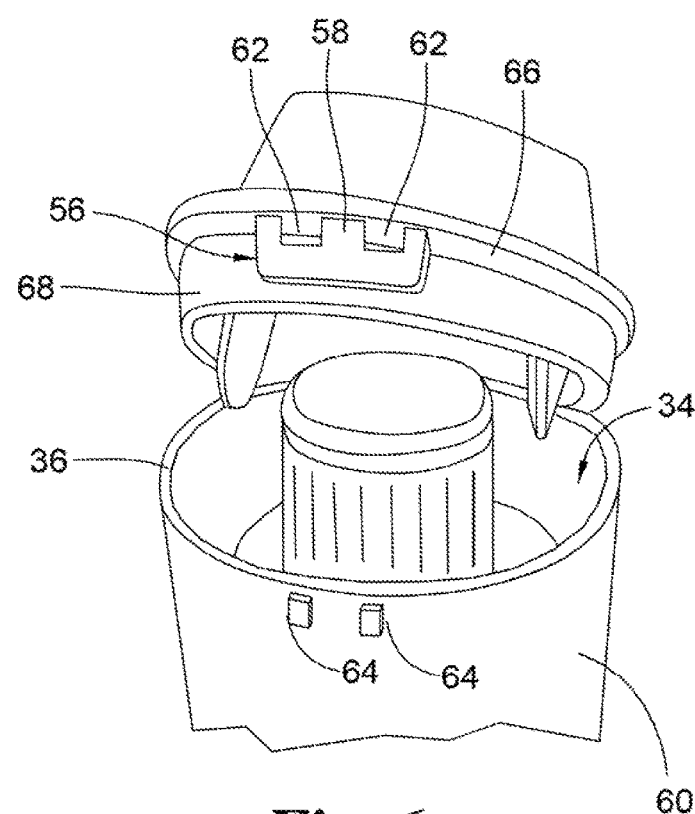
FIG. 6 is a partial perspective view of the medication delivery system shown in FIG. 2, showing details of a latch mechanism of the container and the cap.

Referring to FIG. 6, it is shown that the medication delivery system may include a locking mechanism 56 to hold cap 16 in the closed position with container 14 in the absence of an intended separation of the two components. Any such locking mechanism may be used that provides sufficient security to hold the components in a locked condition, while also permitting a reasonable release of the locking mechanism when desired. In one embodiment, locking mechanism 56 comprises mating latch members or latching mechanism. Latch 58 is attached to cap 16 and extends axially along the container axis when cap 16 is in the closed position. In this position, latch 58 is positioned to be received adjacent an exterior surface 60 of side wall 28. Latch 58 includes a pair of apertures 62. A pair of complementary nubs 64 is formed in exterior surface 60 and are positioned to be received within apertures 62 when cap 16 is placed in its closed position. The latch components and supporting members are sufficiently flexible and resilient for the latch to be opened and closed as required.

Alternative locking and sealing mechanism may also be used. For example, in one embodiment the cap is snap fit with the container. In another embodiment, the cap is secured to the container by a press fit.

Latch 58 may be attached to and depending from an underneath surface of the rim portion 66 of cap 16, as shown in FIG. 2. This allows for the placement of latch 58 to be received adjacent the exterior surface 60 of side wall 28. The radial extent of the rim portion 66 away from the outer surface of the cup shaped body of the cap may be constant. In one example, the radial extent of the rim portion 66 may vary, such as, for example, where the portion 67 of the rim portion 66 that is adjacent the latch 58, may be is radially extended farther than the portion of the rim portion 66 outside of the latch. Extended portion 67 may also serve as a thumb tab to facilitate removal of cap 16 from access opening 34 of container 14. The underneath surface of extended portion 67 may define a thumb contact tab to provide an outwardly-extending surface which may be pressed up and away from container 14 to facilitate removal of the cap from the container. User applies an axial force to the portion 67 to cause portion 67 to pivot due to flexible of material, thereby moving the latch 58 in a manner such that the latch apertures 62 are removed from nubs 64 and the latch 58 clears the nubs 64 to permit the cap to move to its open position.

Figure 7:
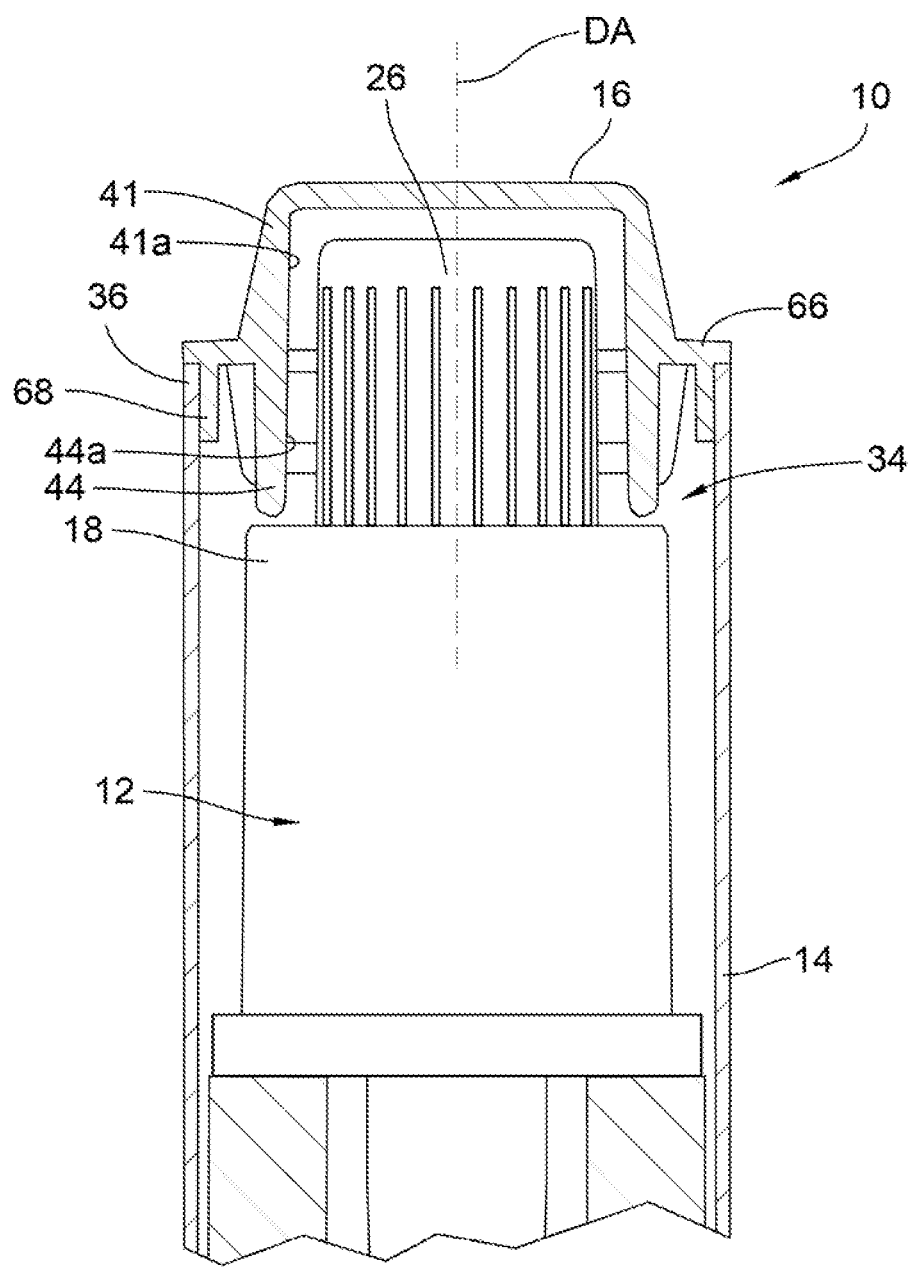
FIG. 7 is a side, partial cross-sectional view of the container of the medication delivery system, showing the cap in the closed position sealed with the container with the device inserted therein.

The medication delivery system is configured to maintain the integrity of the medication administration device and medication from the time they are sealed within the cap and container assembly until the medication administration device is removed and used to dispense the medication. The cap and container are provided with complementary sealing components to ensure a hermetic seal between them. Referring to FIGS. 6 and 7, container 14 includes end wall portion 36 defining access opening 34. Cap 16 includes a circumferential sealing member comprising peripheral axially extending flange 68 which is sized and configured to extend along and closely mate with the interior surface of end wall portion 36 to provide a hermetic seal enclosing the medication administration device in the cap 16 and container 14 assembly. Cap sealing flange 68 extends axially along the container axis CA and is disposed spaced radially inward from the latch 58 to define a gap for receiving the radial thickness of end wall portion 36. The circumferential sealing flange 68 may depend axially from an underneath surface of the rim portion 66. The hold down members 44 are disposed spaced radially inward relative to the flange 68, as shown in FIG. 7. The hold down members 44 are sized to extend axially beyond the bottom wall facing end surface of the flange 68. Flange 68 is shown extending axially beyond the latch 58 of the latching mechanism. A shorter latch relative to the flange wall may reduce the cap opening forces. Latch 58 is shown disposed circumferentially between the two hold down members 44, but across the recess and radially opposite to the hinged connection 50. Hold down members 44 may be about 180 degrees apart, and latch 58 and hinged connection 50 may be about 180 degrees apart.

Figure 8:
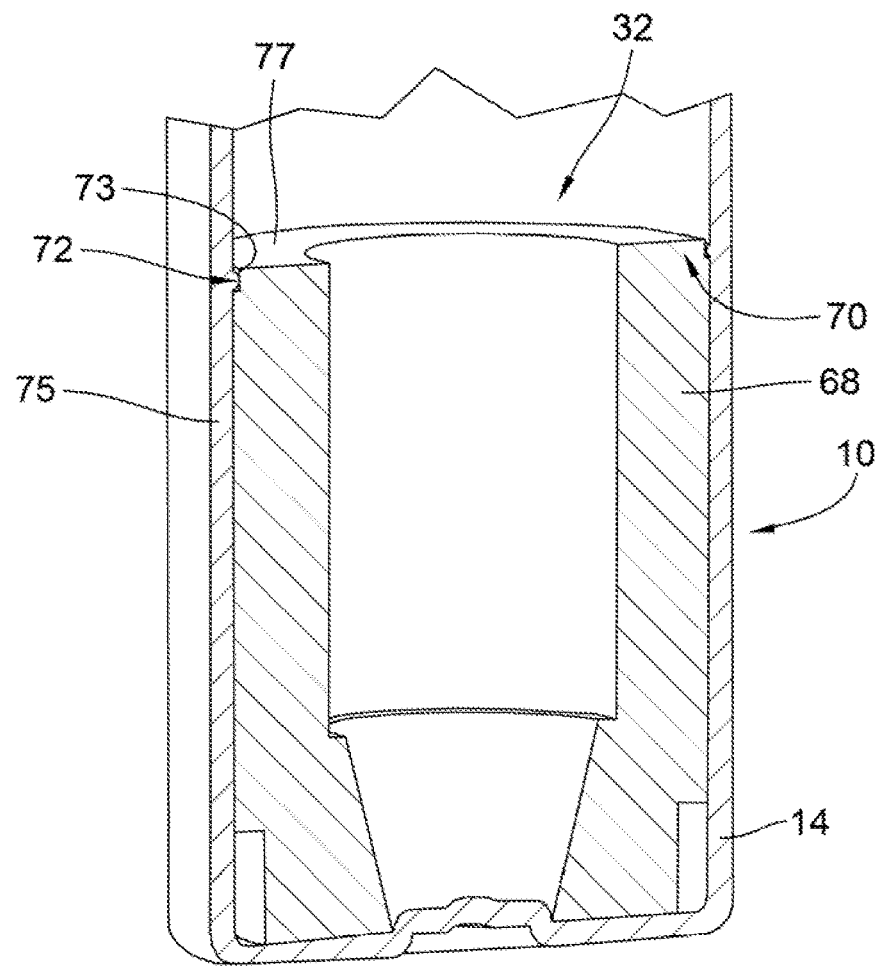
FIG. 8 is a partial, cross-sectional view of the container, showing the interior of the container with a desiccant plug.

The materials used in the cap and container are of a type well known in the art. The materials must provide the desired sealing function. If a living hinge, latch or other features are included, the materials must have sufficient strength, elasticity and resilience to fulfill the functional requirements. A wide variety of materials suitable for use in container 14 and cap 16 are known in the art, and typically include plastics, particularly thermoplastics such as polypropylene and polyethylene Many medications are adversely affected by contact with deleterious levels of moisture. In one embodiment, the medication delivery system contains a moisture sensitive medication and container 14 and/or cap 16 includes a desiccant. Referring to FIG. 8, there is shown a desiccant plug 70 received within container 14. The desiccant plug is configured to fit within container 14 adjacent bottom wall 30, and has an annular shaped body provided with a central cavity 71 to receive medication discharge port 24 of medication administration device 12.

The desiccant plug may be formed, for example, as an injection molded plug of a molecular sieve type, using known materials to absorb moisture that may otherwise degrade the medication. The desiccant plug is sized to comprise enough material to provide sufficient absorption of moisture. For this purpose the desiccant plug may be configured to substantially fill cavity 32 between medication administration device 12 and the interior of side wall 28 of container 14.

Figure 8A:
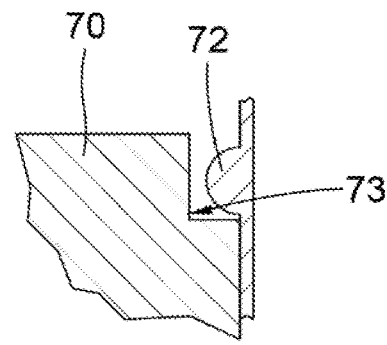
FIG. 8a is a detailed view of the desiccant plug retention mechanism from FIG. 8.

Desiccant plug 70 may be secured within cavity 32 by various means, such as an interference fit. Container 14 may also include a snap fit retention feature in which a radially inward projecting continuous ring or continuous interior shoulder 72 extending from an interior surface of the side wall of the container engages with the axial end surface of desiccant plug 70 once it has been moved a sufficient distance into cavity 32. The desiccant plug 70 may include an annular notch 73 defined along a radially outer surface 75 of the desiccant body, which is shown formed at the intersection of the cap facing axial planar surface 77 of the desiccant body and the radially outer surface of the desiccant body. The annular notch 73 is sized and configured to receive the shoulder 72 when the desiccant is disposed within the container, such as shown in FIG. 8a. Alternatively, the shoulder 72 may be operable to retain an annular shaped desiccant by engaging the cap facing axial planar surface 77 of the desiccant body without the desiccant having the notch 73.

The disclosed medication delivery systems have application, inter alia, with medication administration devices that are pre-filled and provide a medication in dosage form. In particular, the medication administration devices may comprise dispersion devices which, as used herein, are considered to be devices which deliver a medication in a dispersed form, such as in metered aerosol or spray devices. These medication administration devices are pre-filled with the medications in a finished dosage form. Embodiments include devices such as referenced in 68 Fed. Reg. 36,675, 36,676 and 36,680 (Jun. 18, 2003). Exemplary embodiments include intranasal aerosol and spray devices.

The medication delivery systems may comprise a wide range of medication administration devices and medications. The medication delivery system is particularly well suited for use with medication administration devices which are used for administration of powder medications, such as intranasal delivery powders. The medications may be any that can be delivered by the dispersion devices. The medications may be associated with one or more other ingredients, as referenced, for example, at 21 CFR § 314.3.

In an exemplary embodiment, the medication is glucagon. A medication administration device has been developed that provides for the delivery of glucagon in a simple, one-use nasal powder. This provides significant advantages over complicated systems that involve mixing liquid and powder together and then injecting the solution. The use of this medication administration device has been determined to bring blood sugar levels close to normal within 30 minutes of taking the powdered glucagon.

In an embodiment, the medication is intranasal AMG504-1 product (Locemia Solutions) containing 2 mg glucagon in 20 mg dry powder or 3 mg glucagon in 30 mg dry powder, depending on the dose. The nasal powder is administered with a single-use, one-step dispensing device. The tip of the device is inserted in one nostril, and the dose is delivered by simply depressing an actuator connected to a piston that discharges the powder into the nostril. No cooperative measure is required from the patient, as absorption takes place through the nasal mucosa. The glucagon formulation is provided in the medication delivery system as disclosed herein, resulting in a highly effective protection for the viability of both the glucagon and its delivery device.

It is sometimes desirable to provide a training device that allows potential users the opportunity to become familiar with the manner of using a commercial form of a medication delivery system. In one aspect, a modified version of the described medication delivery system is provided which has the same basic structures and functions as the commercial device. However, it is also important that it is not possible to confuse the training device with the commercial device as the training device need not be provided with the same level of refinement. For example, the commercial device is designed to provide a tight seal when the lid is closed upon the container, which is not required for a training device.

Accordingly, the training device is designed in a manner to preclude interchange of parts with the commercial device. For example, the training medication delivery device is configured to prevent its placement inside the commercial container and/or cap. Conversely, the training container and/or cap are configured to preclude reception of the commercial medication delivery device.

In one example, the training device may be sized such that its container and/or cap define a cavity that is too short and/or too narrow to receive the commercial medication device. Similarly, the training medication delivery device may be designed to have a dimension that is not able to be received within the cavity defined by the commercial container and/or cap. It will be appreciated that the container, cap and/or medication delivery device for the training device and the commercial device may be made incompatible in various other ways.

Figure 9:
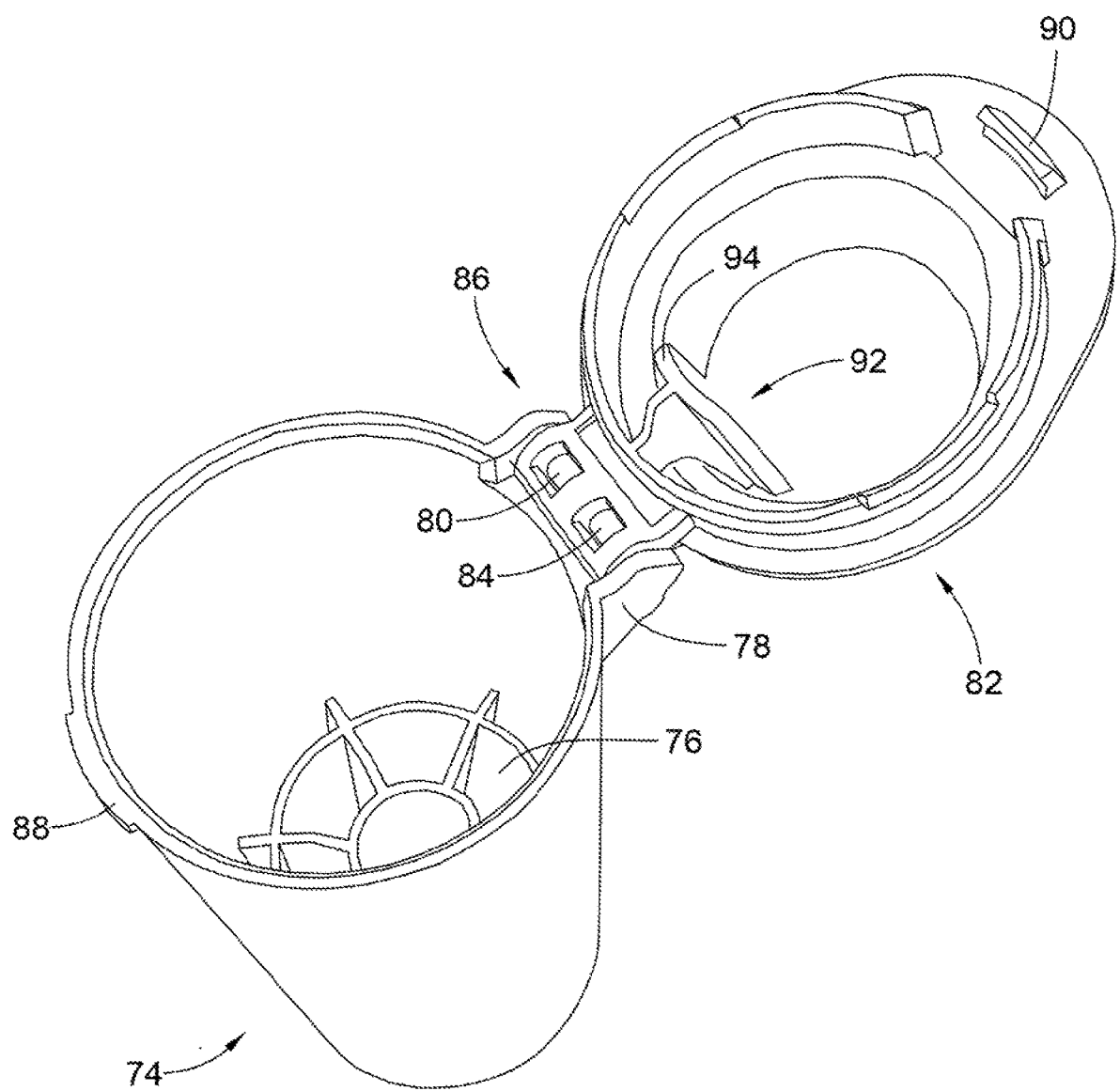
FIG. 9 is a perspective view of a training container with its cap in the open position.
Figure 10:
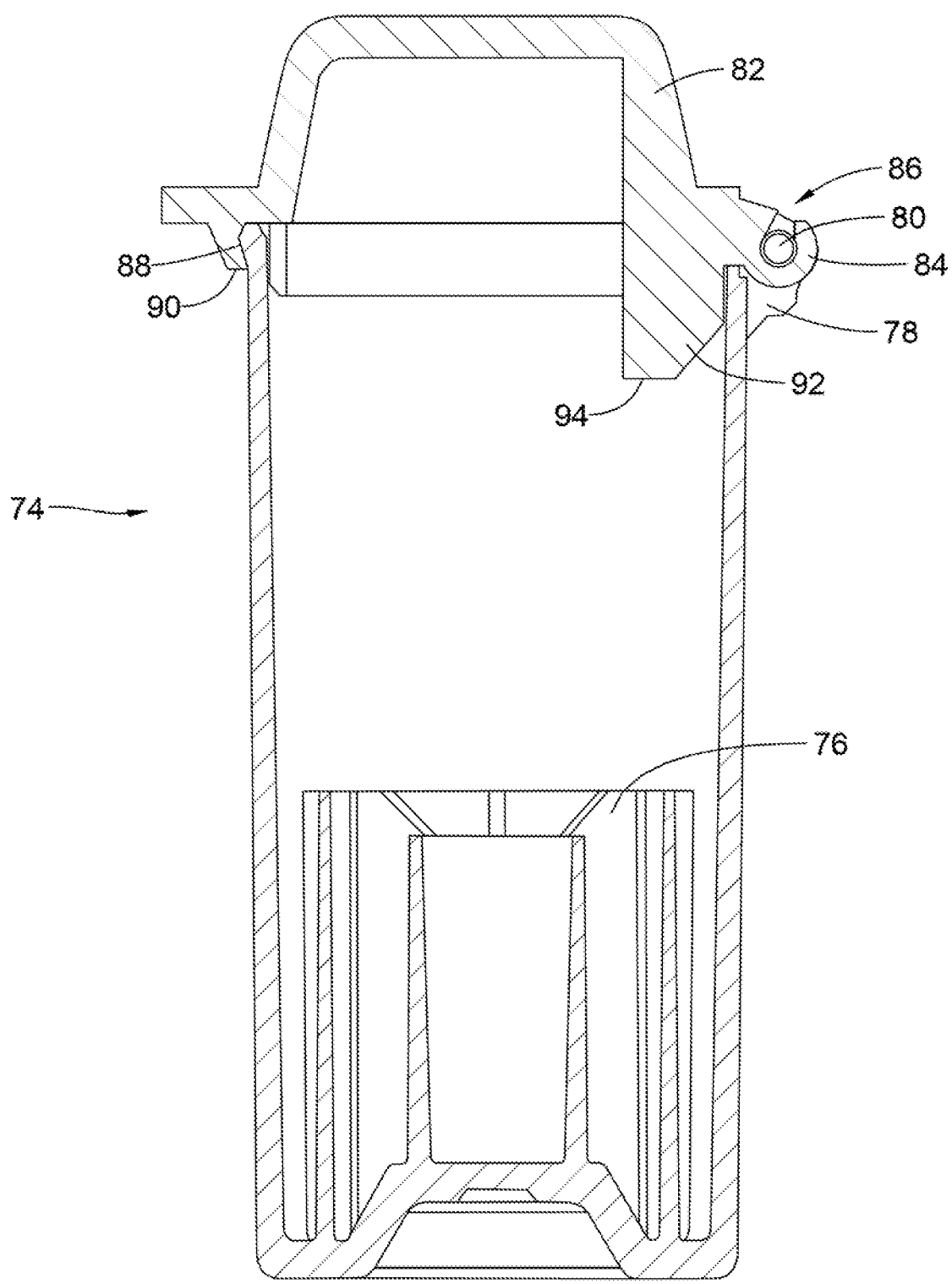
FIG. 10 is a side, cross-sectional view of the training container shown in FIG. 9 with its cap in the closed position.

Referring to FIGS. 9 and 10, there is shown an exemplary training container and cap assembly. Container 74 comprises a cylindrical body including a grid 76 simulating the space occupied by desiccant plug 70 of the prior embodiment. A pair of arms 78 extend outwardly from the top of container 74 and support a hinge pin 80. Cap 82 includes a cup shaped portion 84 defining a channel in which hinge pin 80 is received. Cup shaped portion 84 is formed from a material that is sufficiently flexible as to allow it to be pressed onto hinge pin 80. The combination of the cup shaped portion 84 received over hinge pin 80 provides a hinge 86 connecting cap 82 and container 74.

Container 74 further includes a ridge 88 along the top edge of container 74 in a position opposed to hinge 86. Ridge 88 extends transverse of container 74 and has a slightly convex shape as viewed in cross section. See FIG. 10. Cap 82 includes a flange 90 positioned to be engaged by ridge 88 when cap 82 is in the closed position.

Cap 82 further includes a single hold down member 92 aligned with hinge 86. Hold down member 92 includes a T-shaped end surface 94 positioned to prevent upward displacement of a simulated administration device received in container 74.

Container 74 and cap 82 thereby form a receptacle having variations from the design of the earlier described embodiment. Cap 82, for example, demonstrates a design having a single hold down member, rather than the pair of hold down members 44. Hinge 86 and flange 90 represent alternative designs to the living hinge and latch of the earlier embodiment.

In one aspect, there is provided a medication delivery system comprising two different container and cap assemblies constituting a product system and a training system. The product system is used to contain a medication administration device containing a medication to be delivered to a patient. The training system is used to allow the patient to become familiar with the structures and function of the product system. Instead, it only serves the purpose of allowing a patient to manipulate the training module relative to the container and cap assembly of the training system to learn how the product assembly operates.

The embodiments of FIGS. 2 and 9 are representative of this overall medication delivery system. By way of example, the embodiment of FIG. 2 may serve as the product system and the embodiment of FIG. 9 may serve as the training system.

To obtain maximum effect, the training system includes a training module that simulates the medication delivery device, but does not contain a medication product. However, the training module is configured to operate with the container and cap assembly of the training system in substantially the same as a medication administration device is configured to operate with the contain and cap assembly of the product system.

Thus, the training module may comprise a body having a discharge end defining a simulated medication discharge port and an opposed actuator end including a simulated actuator. The actuator extends out of the actuator end of the body, and the actuator being linearly moveable from an extended position to a depressed position. The training module is configured to be similar to the medication delivery device, although it need not be fully functional, e.g., it need not include an operating actuator. The training container and cap assembly similarly is configured to simulate the container and cap assembly of the product system, but it need not be fully functional, e.g., containing a desiccant.

As previously noted, the components of the product and training systems are configured such that the medication administration device is incompatible with the training container and cap assembly, and the training module is incompatible with the product container and cap assembly. This may be accomplished in a variety of ways. For example, the training module may be provided with an outer diameter that does not fit within the container of the product system. Alternatively, the container of the training system may be made to be too short for the medication administration device such that the cap cannot be closed over the medication administration device. In general, it is sufficient if there is any dimension of the medication administration device that is incompatible with the device being received in the training container with the cap closed.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

Various aspects are described in this disclosure, which include, but are not limited to, the following aspects:

1. A medication delivery system including: a medication administration device comprising a body having a discharge end defining a medication discharge port and an opposed actuator end, the medication administration device including a medication reservoir, the medication administration device further including an actuator for ejecting a medication from the reservoir through the discharge port, the actuator extending out of the actuator end of the body, the actuator being linearly moveable from an extended position to a depressed position, the discharge port being sealed when the actuator is in the extended position and the discharge port being open when the actuator is in the depressed position, the actuator being operable to discharge medication from the reservoir upon axial movement of the actuator from the extended position to the depressed position; a medication received within the reservoir of the medication administration device; a container having an axially extending side wall and a closed bottom wall defining a cavity having an access opening defined by an end wall portion, the medication administration device being received within the cavity with the discharge end adjacent the bottom wall of the container; and a cap coupled to the container, and movable relative to the container between an open position and a closed position, the cap in the closed position sealably engaged with the container to enclose the medication administration device within the cavity, the cap defining one or more hold down axial projections, wherein, when the cap is in the closed position, the one or more hold down axial projections extend axially from the cap in a direction toward the bottom wall and sized to allow at most a predetermined amount of axial movement of the medication administration device in the direction away from the bottom wall, wherein the one or more hold down axial projections are contactable with a non-actuator portion of the medication administration device.

2. The medication delivery system of aspect 1 in which the one or more hold down axial projections is a rigid structure.

3. The medication delivery system of any one of aspects 1-2 in which the body of the medication administration device includes a radially extending circumferential surface surrounding the actuator and facing away from the bottom wall, wherein, when the cap is in the closed position, the one or more hold down axial projections are positioned radially outside the actuator to be contactable against the circumferential surface.

4. The medication delivery system of any one of aspects 1-3 in which the cap having a cup shaped body comprising a cap side wall and defining a recess configured to receive a portion of the actuator, wherein the one or more hold down axial projections extend out beyond the recess.

5. The medication delivery system of aspect 4 in which an interior surface of the cap side wall and an interior surface of the one or more hold down axial projections define a continuous surface.

6. The medication delivery system of any one of aspects 1-5 wherein the one or more hold down axial projections comprises a pair of hold down axial projections extending from the cup shaped body of the cap at radially opposite sides of the cap.

7. The medication delivery system of any one of aspects 1-6 wherein the cap includes an outer rim disposed around the cup shaped body, a circumferential flange depending axially from a bottom wall facing surface of the outer rim, the one or more hold down axial projections disposed spaced radially inward relative to the flange, and extending axially beyond the flange.

8. The medication delivery system of any one of aspects 1-7 in which the cap is coupled to the container by a hinged connection.

9. The medication delivery system of aspect 8 in which the hinged connection is a living hinge.

10. The medication delivery system of aspect 8 in which the cap includes two hold down axial projections, the two hold down projections disposed circumferentially away from one another, the hinged connection disposed circumferentially between the two hold down projections.

11. The medication delivery system of aspect 8 in which the cap includes a single hold down axial projection.

12. The medication delivery system of any one of aspects 1-11 in which the cap includes an outer rim extending radially from the cup shaped body, and a circumferential flange depending axially from a bottom wall facing surface of the outer rim, and the container and the cap comprise a latch member to secure the cap to the container in the closed position, the latch member including a latch extending axially from the outer rim of the cap, wherein said flange extends axially beyond the latch.

13. The medication delivery system of aspect 12 in which the one or more hold down axial projections of the cap comprises two hold down axial projections, the two hold down projections disposed circumferentially away from one another, the hinged connection disposed circumferentially between the two hold down projections, and the latch disposed circumferentially between the two hold down projections radially opposite to the hinged connection.

14. A medication delivery system including: a medication administration device comprising a body having a discharge end defining a medication discharge port and an opposed actuator end, a medication reservoir containing a medication, and an actuator for ejecting the medication from the reservoir through the discharge port, the actuator extending out of the actuator end of the body, the actuator being linearly moveable from an extended position to a depressed position, the discharge port being sealed when the actuator is in the extended position and the discharge port being open when the actuator is in the depressed position, the actuator being operable to discharge medication from the reservoir upon axial movement of the actuator from the extended position to the depressed position, wherein the body of the medication administration device includes a radially extending circumferential surface surrounding the actuator and facing away from the bottom wall; and a container comprising an axially extending side wall and a closed bottom wall defining a cavity having an access opening defined by an end wall portion, the medication administration device being received within the cavity with the discharge end adjacent the bottom wall of the container, a cap hingedly coupled to the container, the cap movable relative to the container between an open position and a closed position, the cap in the closed position sealably engaged with the container to enclose the medication administration device within the cavity, and a desiccant disposed within the cavity, wherein the cap defines a pair of hold down axial projections, wherein, when the cap is in the closed position, the hold down axial projections extend axially from the cap in a direction toward the bottom wall and sized to allow at most a predetermined amount of axial movement of the medication administration device in the direction away from the bottom wall, wherein each of the hold down axial projections have a contact end surface contactable with the circumferential surface of said device, radially outside the actuator of the medication administration device, wherein the hold down axial projections are configured to allow each of the contact end surfaces to maintain its relative axial position and radial position relative to the cap and the circumferential surface of said device 15. The medication delivery system of aspect 14 in which the container includes a continuous inner ring disposed radially inward from an interior surface of the side wall of the container, the inner ring axially spaced from the bottom wall at a distance to securely retain the desiccant between the inner ring and the bottom wall.

16. The medication delivery system of aspect 15 in which the desiccant includes an annular notch defined along a radially outer surface of the desiccant, the annular notch configured to receive the inner ring when the desiccant is disposed within the container.

17. The medication delivery system of any one of aspects 1-16 in which the medication administration device is an air dispersion device.

18. The medication delivery system of any one of aspects 1-17 in which the medication is an intranasal delivery powder.

19. The medication delivery system of aspect 18 in which the powder is glucagon.

20. A method for providing a medication delivery system containing a glucagon composition, the method including: positioning a medication administration device within a container, the medication administration device including a body having a discharge end defining a medication discharge port and an opposed actuator end, the medication administration device including a medication reservoir containing a glucagon medication, the medication administration device further including an actuator for ejecting a medication from the reservoir through the discharge port, the actuator extending out of the actuator end of the body, the actuator being linearly moveable from an extended position to a depressed position, the discharge port being sealed when the actuator is in the extended position and the discharge port being open when the actuator is in the depressed position, the actuator being operable to discharge the glucagon medication from the reservoir upon axial movement of the actuator from the extended position to the depressed position; the container having a side wall and a closed bottom wall defining a cavity having an access opening defined by an end wall portion, the cavity receiving the medication administration device within the cavity with the discharge end adjacent the bottom wall of the container; and sealing a cap to the container to provide a hermetic seal enclosing the medication administration device within the cavity, the cap defining one or more hold down axial projections positioned and configured to interfere with movement of the medication administration device to allow at most a predetermined amount of movement of the medication administration device in the direction away from the bottom wall without the actuator contacting an axial end surface of the cap.

21. A medication container and cap assembly for containing a medication administration device, the medication administration device including a body having a discharge end defining a medication discharge port and an opposed actuator end, the medication administration device including a medication reservoir containing a glucagon medication, the medication administration device further including an actuator for ejecting the glucagon medication from the reservoir through the discharge port, the actuator extending out of the actuator end of the body, the actuator being linearly moveable from an extended position to a depressed position, the discharge port being sealed when the actuator is in the extended position and the discharge port being open when the actuator is in the depressed position, the actuator being operable to discharge the glucagon medication from the reservoir upon axial movement of the actuator from the extended position to the depressed position, the assembly including: a container having a side wall and a closed bottom wall defining a cavity having an access opening defined by an end wall portion, the cavity being sized and configured to receive the medication administration device, the medication administration device being receivable within the cavity with the discharge end adjacent the bottom wall of the container; and a cap coupled to the container by a hinged connection, and configured to mate with the container when in a closed position and provide a hermetic seal to enclose the medication administration device inserted within the cavity, the cap defining a pair of hold down members positioned and configured to interfere with movement of the medication administration device to allow at most a predetermined amount of movement of the medication administration device in the direction away from the bottom wall, the hold down members disposed circumferentially away from one another, the hinge connection disposed circumferentially between the two hold down members.

22. The assembly of aspect 21 in which the container side wall is sized to allow an end portion of the actuator to extend out beyond the container side wall through the open end of the container, the cap having a cup-shaped body defining a recess configured to receive the end portion of the actuator, wherein an interior surface of the cup-shaped body that faces the recess and an interior surface of each of the hold down members where the hold down members extend from the cup-shaped body define a continuous surface.

23. The assembly of aspect 22 in which the desiccant is configured to fit within the container adjacent the bottom wall, the desiccant including an annular shaped body with a central cavity configured to receive the medication discharge port of the medication administration device therein, the container including an inner ring disposed radially from an interior surface of the side wall of the container, and the desiccant includes an annular notch defined along a radially outer end of the annular shaped body that faces away from the bottom wall, the annular notch configured to receive the inner ring when the desiccant is disposed within the container.

24. A training module for use in a medication delivery system including: a training module including a body having a discharge end defining a simulated medication discharge port and an opposed actuator end including a simulated actuator, the actuator extending out of the actuator end of the body, a training container having a side wall and a closed bottom wall defining a cavity having an access opening defined by an end wall portion, the cavity being sized and configured to receive the training module, the training module being received within the cavity with the discharge end adjacent the bottom wall of the container; and a training cap hingedly attached to the training container, the training cap mating with the training container and enclosing the training module within the cavity, the training cap defining one or more hold down members positioned and configured to interfere with movement of the training module to allow at most a predetermined amount of movement of the training module in the direction away from the bottom wall, each of the one or more hold down members including a projection extending from the training cap in a direction toward the bottom wall.

25. A medication delivery system including: a medication administration device including a body having a discharge end defining a medication discharge port and an opposed actuator end, the medication administration device including a medication reservoir, the medication administration device further including an actuator for ejecting a medication from the reservoir through the discharge port, the actuator extending out of the actuator end of the body, the actuator being linearly moveable from an extended position to a depressed position, the discharge port being sealed when the actuator is in the extended position and the discharge port being open when the actuator is in the depressed position, the actuator being operable to discharge medication from the reservoir upon axial movement of the actuator from the extended position to the depressed position; medication received within the reservoir of the medication administration device; a product container having a side wall and a closed bottom wall defining a cavity having an access opening defined by an end wall portion, the cavity being sized and configured to receive the medication administration device, the medication administration device being received within the cavity with the discharge end adjacent the bottom wall of the container; a product cap attached to the container, the product cap mating with the container and providing a hermetic seal enclosing the medication administration device within the cavity, the product cap defining one or more hold down members positioned and configured to interfere with movement of the medication administration device to allow at most a predetermined amount of movement of the medication administration device in the direction away from the bottom wall, each of the one or more hold down members including a projection extending from the cap in a direction toward the bottom wall, a training module including a body having a discharge end defining a simulated medication discharge port and an opposed actuator end including a simulated actuator, the simulated actuator extending out of the actuator end of the body of the training module, a training container having a side wall and a closed bottom wall defining a cavity having an access opening defined by an end wall portion, the cavity being sized and configured to receive the training module, the training module being received within the cavity with the discharge end adjacent the bottom wall of the container; and a training cap attached to the training container, the training cap mating with the training container and enclosing the training module within the cavity, the training cap defining one or more hold down members positioned and configured to interfere with movement of the training module to allow at most a predetermined amount of movement of the training module in the direction away from the bottom wall, each of the one or more hold down members including a projection extending from the training cap in a direction toward the bottom wall, the medication delivery device including a dimension that is incompatible with it being received within the training container with the training cap closed.

26. The medication delivery system of aspect 25 in which the training module includes a dimension that is incompatible with it being received within the product container with the product cap closed.

What is claimed is:

1. A medication delivery system comprising:
a medication administration device comprising a body having a discharge end defining a medication discharge port and an opposed actuator end, the medication administration device including a medication reservoir, the medication administration device further including an actuator for ejecting a medication from the reservoir through the discharge port,
the actuator extending out of the actuator end of the body,
the actuator being linearly moveable from an extended position to a depressed position, the discharge port being sealed when the actuator is in the extended position and the discharge port being open when the actuator is in the depressed position, the actuator being operable to discharge the medication from the reservoir upon axial movement of the actuator from the extended position to the depressed position;
said medication received within the reservoir of the medication administration device;
a container having an axially extending side wall and a closed bottom wall defining a cavity having an access opening defined by an end wall portion, the medication administration device being received within the cavity with the discharge end adjacent the closed bottom wall of the container, and a desiccant disposed within the cavity, the desiccant having an annular shape to define an opening to receive the medication discharge port of the medication administration device, in which the container includes a continuous interior shoulder disposed radially inward from an interior surface of the axially extending side wall, the continuous interior shoulder axially spaced from the closed bottom wall at a distance to securely retain the desiccant between the continuous interior shoulder and the closed bottom wall, in which the desiccant includes an annular notch defined along a radially outer surface of the desiccant, the annular notch configured to receive the continuous interior shoulder when the desiccant is disposed within the container; and
a cap coupled to the container, and movable relative to the container between an open position and a closed position, the cap in the closed position is sealably engaged with the container to enclose the medication administration device within the cavity,
the cap defining one or more hold down members, wherein, when the cap is in the closed position, the one or more hold down members extends axially from the cap in a direction toward the closed bottom wall and is sized to allow at most a predetermined amount of axial movement of the medication administration device in the direction away from the closed bottom wall, wherein the one or more hold down members is contactable with a non-actuator portion of the medication administration device.

2. The medication delivery system of claim 1 in which the one or more hold down members is a rigid structure.

3. The medication delivery system of claim 2 in which the body of the medication administration device includes a radially extending circumferential surface surrounding the actuator and facing away from the closed bottom wall, wherein, when the cap is in the closed position, the one or more hold down members is positioned radially outside the actuator to be contactable against the circumferential surface.

4. The medication delivery system of claim 3 in which the cap having a cup shaped body comprising a cap side wall and defining a recess configured to receive a portion of the actuator, wherein the one or more hold down axial members extends out beyond the recess.

5. The medication delivery system of claim 4 in which an interior surface of the cap side wall and an interior surface of the one or more hold down members define a continuous surface.

6. The medication delivery system of claim 4 wherein the one or more hold down members comprises a pair of hold down axial projections extending from the cup shaped body of the cap at radially opposite sides of the cap.

7. The medication delivery system of claim 4 wherein the cap includes an outer rim disposed around the cup shaped body, a circumferential flange depending axially from a bottom wall facing surface of the outer rim, the one or more hold down members disposed spaced radially inward relative to the flange, and extending axially beyond the flange.

8. The medication delivery system of claim 2 in which the cap is coupled to the container by a hinged connection.

9. The medication delivery system of claim 8 in which the hinged connection is a living hinge.

10. The medication delivery system of claim 8 in which the one or more hold members includes two hold down members, the two hold down members disposed circumferentially away from one another, the hinged connection disposed circumferentially between the two hold down members.

11. The medication delivery system of claim 8 in which the one or more hold members includes a single hold down member.

12. The medication delivery system of claim 3 in which the cap includes an outer rim extending radially from the cup shaped body, and a circumferential flange depending axially from a bottom wall facing surface of the outer rim, and the container and the cap comprise a latch member to secure the cap to the container in the closed position, the latch member including a latch extending axially from the outer rim of the cap, wherein said flange extends axially beyond the latch.

13. The medication delivery system of claim 12 in which the one or more hold down members of the cap comprises two hold down members, the two hold down members disposed circumferentially away from one another, the hinged connection disposed circumferentially between the two hold down members, and the latch disposed circumferentially between the two hold down members radially opposite to the hinged connection.

14. A medication delivery system comprising:
a medication administration device comprising a body having a discharge end defining a medication discharge port and an opposed actuator end, a medication reservoir containing a medication, and an actuator for ejecting the medication from the reservoir through the discharge port, the actuator extending out of the actuator end of the body, the actuator being linearly moveable from an extended position to a depressed position, the discharge port being sealed when the actuator is in the extended position and the discharge port being open when the actuator is in the depressed position, the actuator being operable to discharge said medication from the reservoir upon axial movement of the actuator from the extended position to the depressed position; and
a container comprising an axially extending side wall and a closed bottom wall defining a cavity having an access opening defined by an end wall portion, the medication administration device being received within the cavity with the discharge end adjacent the bottom wall of the container, a cap hingedly coupled to the container, the cap movable relative to the container between an open position and a closed position, the cap in the closed position is sealably engaged with the container to enclose the medication administration device within the cavity, and a desiccant disposed within the cavity, the desiccant having an annular shape to define an opening to receive the medication discharge port of the medication administration device, wherein the body of the medication administration device includes a radially extending circumferential surface surrounding the actuator and facing away from the closed bottom wall,
in which the container includes a continuous interior shoulder disposed radially inward from an interior surface of the axially extending side wall of the container, the continuous interior shoulder axially spaced from the closed bottom wall at a distance to securely retain the desiccant between the continuous interior shoulder and the closed bottom wall, in which the desiccant includes an annular notch defined along a radially outer surface of the desiccant, the annular notch configured to receive the continuous interior shoulder when the desiccant is disposed within the container,
wherein the cap defines a pair of hold down members, wherein, when the cap is in the closed position, the hold down members extend axially from the cap in a direction toward the closed bottom wall and sized to allow at most a predetermined amount of axial movement of the medication administration device in the direction away from the closed bottom wall, wherein each of the hold down members has a contact end surface contactable with the circumferential surface of said medication administration device, radially outside the actuator of the medication administration device, wherein the hold down members are configured to allow each of the contact end surfaces to maintain its relative axial position and radial position relative to the cap and the circumferential surface of said device.

15. The medication delivery system of claim 14 in which the medication administration device is an air dispersion device.

16. The medication delivery system of claim 15 in which the medication is an intranasal delivery powder.

17. The medication delivery system of claim 16 in which the powder is glucagon.

18. A method for providing a medication delivery system containing a glucagon composition, the method comprising:
positioning a medication administration device within a container,
the medication administration device comprising a body having a discharge end defining a medication discharge port and an opposed actuator end, the medication administration device including a medication reservoir containing a glucagon medication, the medication administration device further including an actuator for ejecting said glucagon medication from the reservoir through the discharge port, the actuator extending out of the actuator end of the body, the actuator being linearly moveable from an extended position to a depressed position, the discharge port being sealed when the actuator is in the extended position and the discharge port being open when the actuator is in the depressed position, the actuator being operable to discharge the glucagon medication from the reservoir upon axial movement of the actuator from the extended position to the depressed position;

the container having a side wall and a closed bottom wall defining a cavity having an access opening defined by an end wall portion, the cavity receiving the medication administration device within the cavity with the discharge end adjacent the closed bottom wall of the container, and a desiccant disposed within the cavity, the desiccant having an annular shape to define an opening to receive the medication discharge port of the medication administration device, in which the container includes a continuous interior shoulder disposed radially inward from an interior surface of the side wall, the continuous interior shoulder axially spaced from the closed bottom wall at a distance to securely retain the desiccant between the continuous interior shoulder and the closed bottom wall, in which the desiccant includes an annular notch defined along a radially outer surface of the desiccant, the annular notch configured to receive the continuous interior shoulder when the desiccant is disposed within the container; and sealing a cap to the container to provide a hermetic seal enclosing the medication administration device within the cavity, the cap defining one or more hold down members positioned and configured to interfere with movement of the medication administration device to allow at most a predetermined amount of movement of the medication administration device in the direction away from the closed bottom wall without the actuator contacting an axial end surface of the cap.

19. A medication container and cap assembly for containing a medication administration device, the medication administration device comprising a body having a discharge end defining a medication discharge port and an opposed actuator end, the medication administration device including a medication reservoir containing a medication, the medication administration device further including an actuator for ejecting the medication from the reservoir through the discharge port, the actuator extending out of the actuator end of the body, the actuator being linearly moveable from an extended position to a depressed position, the discharge port being sealed when the actuator is in the extended position and the discharge port being open when the actuator is in the depressed position, the actuator being operable to discharge the medication from the reservoir upon axial movement of the actuator from the extended position to the depressed position, the assembly comprising:

a container having a side wall and a closed bottom wall defining a cavity having an access opening defined by an end wall portion, the cavity being sized and configured to receive the medication administration device, the medication administration device being receivable within the cavity with the discharge end adjacent the closed bottom wall of the container, and a desiccant disposed within the cavity, the desiccant having an annular shape to define an opening to receive the medication discharge port of the medication administration device, in which the container includes a continuous interior shoulder disposed radially inward from an interior surface of the side wall, the continuous interior shoulder axially spaced from the closed bottom wall at a distance to securely retain the desiccant between the continuous interior shoulder and the closed bottom wall, in which the desiccant includes an annular notch defined along a radially outer surface of the desiccant, the annular notch configured to receive the continuous interior shoulder when the desiccant is disposed within the container; and a cap coupled to the container by a hinged connection, and configured to mate with the container when in a closed position and provide a hermetic seal to enclose the medication administration device inserted within the cavity, the cap defining a pair of hold down members positioned and configured to interfere with movement of the medication administration device to allow at most a predetermined amount of movement of the medication administration device in the direction away from the closed bottom wall, the hold down members disposed circumferentially away from one another, the hinge connection disposed circumferentially between the two hold down members.

20. The assembly of claim 19 in which the container side wall is sized to allow an end portion of the actuator to extend out beyond the container side wall, the cap having a cup shaped body defining a recess configured to receive the end portion of the actuator, each of the hold down members extending from the cup shaped body, wherein an interior surface of the cup shaped body that faces the recess and an interior surface of the hold down members define a continuously smooth surface.

21. The medication delivery system of claim 1 in which the medication administration device is an air dispersion device.

22. The medication delivery system of claim 21 in which the medication is an intranasal delivery powder.

23. The medication delivery system of claim 22 in which the powder is glucagon.

* * * * *

UNITED STATES PATENT AND TRADEMARK OFFICE
CERTIFICATE OF CORRECTION

| | |
|---|---|
| PATENT NO. | : 10,765,602 B1 |
| APPLICATION NO. | : 16/578498 |
| DATED | : September 8, 2020 |
| INVENTOR(S) | : Jaime Ray Arnett and Andrew Thomas Snow |

Page 1 of 1

It is certified that error appears in the above-identified patent and that said Letters Patent is hereby corrected as shown below:

In the Claims

In Column 17, Line 16, in Claim 4, after "down" delete "axial".

Signed and Sealed this
First Day of December, 2020

Andrei Iancu
*Director of the United States Patent and Trademark Office*